United States Patent [19]

Hofmann

[11] Patent Number: 5,690,107
[45] Date of Patent: Nov. 25, 1997

[54] METHOD FOR POSITIONING AND MARKING A PATIENT AT A DIAGNOSTIC APPARATUS

[75] Inventor: Karsten Hofmann, Bleckede, Germany

[73] Assignee: Lap GmbH Laser Applikationen, Luneberg, Germany

[21] Appl. No.: 637,229

[22] Filed: Apr. 24, 1996

[30] Foreign Application Priority Data

Jul. 8, 1995 [DE] Germany ............. 195 24 951.8

[51] Int. Cl.$^6$ ............................................. A61B 6/00
[52] U.S. Cl. ............................. 128/653.1; 378/206
[58] Field of Search ............. 128/653.1, 660.03; 364/413.26; 378/206

[56] References Cited

U.S. PATENT DOCUMENTS

| | | | |
|---|---|---|---|
| 5,143,076 | 9/1992 | Hardy et al. | 128/664 |
| 5,320,111 | 6/1994 | Livingston | 128/754 |
| 5,391,139 | 2/1995 | Edmundson | 600/7 |
| 5,411,026 | 5/1995 | Carol | 128/660.03 |
| 5,447,154 | 9/1995 | Cinquin et al. | 128/653.1 |

Primary Examiner—Francis Jaworski
Assistant Examiner—Derrick Fields
Attorney, Agent, or Firm—Vidas, Arrett & Steinkraus, P.A.

[57] ABSTRACT

The invention related to positioning and marking a patient at a diagnostic apparatus, for example before and after a fluoroscopic examination in a computer tomograph comprising at least four line lasers being movably supported for travelling along a respective axis, two line lasers being arranged above a patient placed on a movable table projecting a sagittal line and a transverse line on the body of the patient and two further line lines arranges sidewards of the table each projecting a line along the body axis sidewards on the body, further comprising numerically controlled drive means for moving the line lasers to adjust the projected lines in a transverse direction and comprising a positioning control device, controlling the drive means and a manually operated input device for supplying the coordinates, the location and extension of the radiation zone as determined by the computer tomograph for being supplies to the control device, and projecting orthogonal coordinate axes on the patient for marking the projection of a radiation zone on the skin.

5 Claims, 3 Drawing Sheets

METHOD FOR POSITIONING AND MARKING A PATIENT AT A DIAGNOSTIC APPARATUS

The present invention relates to a method for positioning and marking a patient at a diagnostic apparatus, for example before and after a fluoroscopic examination in a computer tomograph has been made. Still further, the invention relates to a method for marking a zone to be irradiated, i.e. a radiation zone.

BACKGROUND OF THE INVENTION

In radiation therapy it is required to precisely direct the beam of a radiation source onto a patient body's radiation zone to be irradiated and this should be done in a reproducible manner. For reducing the strain acting on zones not to be treated, the source of radiation is pivoted about a so-called isocenter so that the center of the radiation zone receives always the same dosis rate, while adjacent zones not to be treated receive a substantially reduced rate. Therefore, with respect to the radiation apparatus a patient should be positioned such that the center of the radiation zone coincides with the isocenter of the radiation apparatus. The position of the radiation zone may be determined by appropriate diagnostic methods, for example by a computer tomograph (CT). To accomplish this, not only the coordinates of the center of the radiation zone are essential, but further the extension of the zone as well as the scope to be subjected to radiation. The focal point of the radiation apparatus is generally located between the radiation source and the patient's body. This results in a diverging radiation covering a more or less large area on the skin depending on the patient's body dimensions. Using a mask tends to reduce this area.

For appropriately positioning a patient with respect to the radiation apparatus, it is required to indicate or, respectively, to mark the position of the radiation area. It is a conventional technique to precisely position the patient laying on a table by means of a linear laser system stationarily arranged in a radiation room before the patient will be moved to the radiation apparatus.

The coordinates of the radiation zone will be determined by means of a CT, for example. The coordinates will be marked on the skin of the patient such that the center of the tumor is located in the isocenter of the radiation apparatus, when the patient is oriented with respect thereto.

The radiation zone must be selected such that the tumor located inside the body is fully subjected to the radiation while the ajacent tissue is spared as far as possible. Accordingly, it is useful to project the radiation zone on the skin such that the projection of the laser rays extends along the direction of the beam emitted from the radiation apparatus (beam's eye view) when planning the therapy as in this way the skin surface and the tumor inside the body are aligned along an axis. Further, the divergence of the radiation source can be considered as otherwise the lines projected from the laser devices may be distorted by the body profiles.

OBJECT AND SUMMARY OF THE INVENTION

It is a first object of the present invention to provide a method for positioning and marking a patient by means of a computer tomograph.

It is a second object of the present invention to provide a method for marking a radiation zone.

According to the invention the first object referred to is solved by the features of claim 1, while the second object referred to is solved by the features of claim 3.

To accomplish the first method referred to, at least four line lasers will be utilized which are arranged in a room to be moved along an axis. At least a pair of laser devices arranged above the patient generates a so-called sagittal line and a so-called transverse line. Preferably a pair of line lasers will be used for generating a common transverse line substantially surrounding the patient's body. By moving the line lasers the transverse line may be moved along the sagittal axis, for example, while the sagittal line can be moved along the transverse axis. Two further laser devices each project a line along the body axis from either side. These laser devices may be moved up and down vertically in synchronism to the axes referred to. The lines referred to are bounderies of light planes, which are emitted from the laser devices. The beam planes intersect in a point of an orthogonal coordinate system. In marking a radiation zone one tends to provide that the point of origin of the coordinate system coincides with the center of the radiation zone such that this center may be aligned to the isocenter of the radiation apparatus.

By means of a positioning control device the numerically controlled drive means for the laser devices will be controlled to perform the desired motion. The amounts of motion depends on the control data which is received by the control device through a manually actuated input device. This data will be determined by means of the diagnostic device, for example a CT. Thus the coordinates of the center of the radiation zone (tumor center) can be determined by means of the CT. However, the coordinates referring to the extension of the tumor along the three axes can be also determined. When the coordinates have been determined, they can be supplied to the controller through the input device and the controller controls driving the projected lines to the desired position. In addition to the coordinates of the tumor, further data may be supplied such as the divergence of the radiation device. The divergence specifies the radiation zone on the skin or of the tumor. This zone further depends on the distance between the skin surface and the focal point of the radiation device. By adjusting the lines to the desired positions, not only the isocenter for the radiation may be thus determined, but also the projection of the geometrical extension of the tumor on the skin surface along the three axes, for example. Additionally, the entry field limits for the distance between the focal point and the skin surface may be determined and marked as well as any other positions may be determined after supplying individual coordinates.

By using a separate input device, the method according to the invention is completely independent of the respective design of the CT or any diagnostic device.

It is conventional to stationarily arrange the radiation source with respect to the body axis of the patient, while it is rotatable in a transverse plane. Accordingly, the focal point of the radiation device travels in a flying circle around the isocenter. The patient laying on a mobile table can be moved to any desired position with respect to the radiation device and thus the tumor can be moved into the isocenter. To orient the radiation source onto the tumor and to control the radiation rate, it is advantageous in accomplishing a desired adjustment of the radiation source or a desired path of the radiation beams to mark the radiation area on the skin. Preferably, this marking is accomplished by a further method which follows after the coordinates of the tumor with respect to its location and its extension have been determined by means of a CT, for example.

After determining the location and extension of the radiation zone of the patient, the distance between the focus of the radiation device and the center of the radiation zone, the radiation direction and the divergence of the radiation will be selected or calculated. Accordingly, the coordinates of the focus and the direction of the radiation beams are defined. Thereafter, a first line laser beam will be generated intersecting the focus and its prolongation being tangent to the radiation zone. This laser beam corresponds to one of the boundary beams in obtaining an ideal radiation. Furthermore a second line laser beam will be generated alike intersecting the focus and being tangent to the radiation zone at a substantially opposite location. This line laser beam corresponds to a further desired boundary beam of the radiation. Together with further beams of the respective line laser beam plane two marking lines will be generated this way on the skin of the patient. The distance therebetween in the plane defined by the pair of line laser beams corresponds to the extension of the radiation zone on the skin. The distance of the marking lines and the position of the radiation area along the marking lines may be indicated by a line laser representing the orientation of the plane defined by both the line laser beams as a further marking line on the skin. The extension of the radiation zone is then defined by the distance between the points in which the further marking line intersects the first pair of marking lines.

Preferably, in performing the method, the line lasers will be pivoted about an axis parallel to said sagittal axis. Thus, the beam planes may be oriented such that the beams in the transverse planes do not extend parallel or orthogonal with respect to the axes of the coordinate system, but can be rather oriented under any desired angle with respect to the system or axis of travelling.

Moreover, the line lasers may be rotated about an axis extending parallel to the line beams in the line beam plane. In this way it can be accomplished that a line laser generates a line being parallel with respect to the transverse axis on the skin of the patient instead of a line parallel with respect to the sagittal axis.

A substantial advantage of the method according to the invention is the fact that the line laser beams extend like the boundary beams of the radiation beams, i.e. intersect the focus of the radiation device, i.e. the divergence of the radiation beams and the line laser beams is the same. Accordingly, the simulation of the radiation beams by the line laser beams is independent of the distance between the focus and the skin surface of the patient, i.e. parallax errors are eliminated.

In particular in using a CT for diagnostic purposes the degrees of freedom of the line lasers are advantageous since the table for the patient may be only moved along two axes at a CT, i.e. in a forward and rearward direction as well as upwards and downwards.

A further advantage should be seen in the fact that the mechanical and controlling expenditure of the method are less in contrast to providing the line lasers freely movable in space in order to simulate the beam direction of the radiation source. Preferably, the positioning and the angular adjustment of the line lasers will be accomplished by an algorithm calculated by a processor calculating the direction of the line laser beams based on the data determined by the diagnosis and therapy. These data may be supplied from the therapy planning system to the processor for the positioning control or via the input device to the controller. The positioning controller controls the numerically controlled servos for the line laser to accomplish the desired motions.

BRIEF DESCRIPTION OF THE DRAWINGS

Other objects will become more readily apparent from a review of the following description which makes reference to the accompanying drawings.

DETAILED DESCRIPTION

Figure 1:
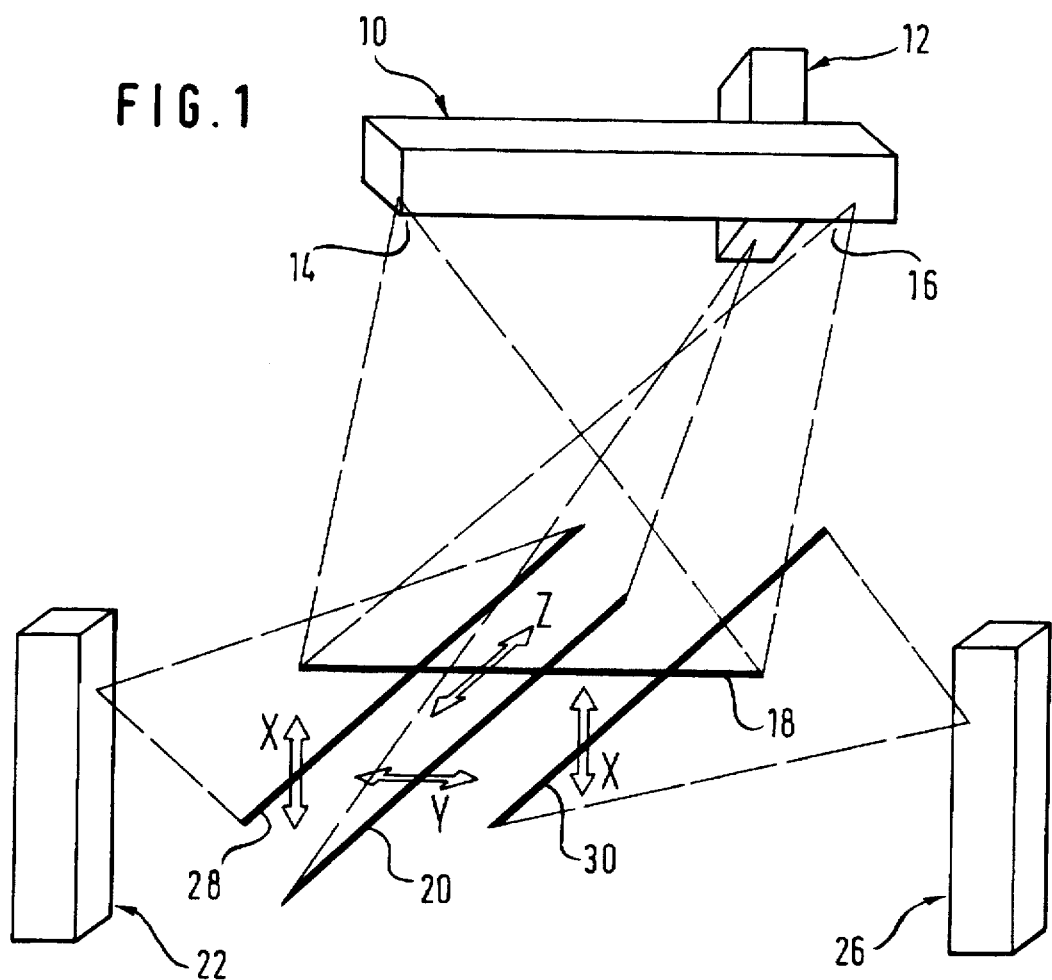
FIG. 1 is a schematic diagram showing a portion of an apparatus for conducting the method for positioning and marking a patient at diagnostic devices.

Referring now to FIG. 1 there are schematically shown two laser devices 10, 12 fixed to the ceiling of a room which further accommodates a computer tomograph (not shown) as well as a mobile table for moving the patient to and from the CT, wherein the table is driven by means of a numerically controlled drive motor. The laser device 10 comprises a pair of lasers 14, 16 for generating a common transverse line 18 approximately extending around the body (not shown) of the patient.

The laser device 12 generates a sagittal line, whereby the patient placed on the table may be oriented with respect to this line. A pair of side laser devices 22, 26 each project a line along the body axis on either side of the body. These lines are marked 28 and 30.

The laser devices 10, 12, 22 and 26 can be adjusted along an axis by means of numerically controlled motors (not shown) such that the transversal line 18 can be moved along the sagittal axis (Z-axis), the sagittal line 20 along the transverse axis (Y-axis) and the side lines 28,30 along the X-axis.

The plane in which the lines 18, 20, 28 and 30 extend intersect in a zero point of the coordinates system, which can be moved by driving the laser devices including the lines which may be individually moved.

Figure 2:
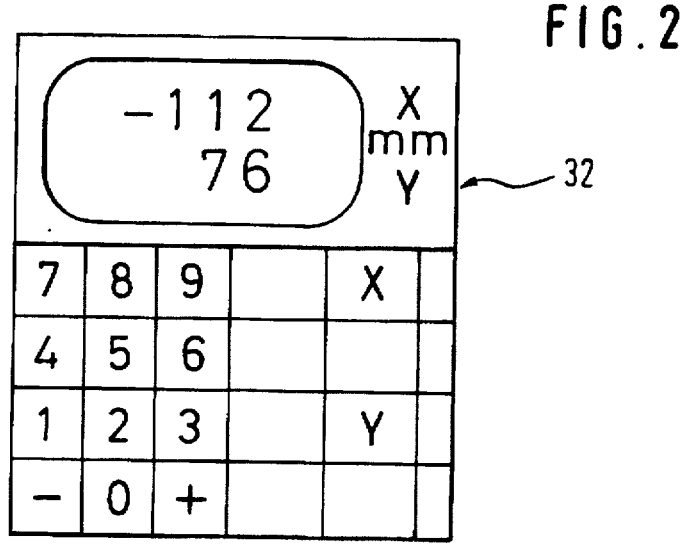
FIG. 2 is a schematic view of an operating module for a controller used in the device of FIG. 1.

The drive motors (not shown) are controlled by a positioning controller (not shown) receiving command data from an input de-vice 32 of which the keyboard is shown in FIG. 2.

Figure 3:
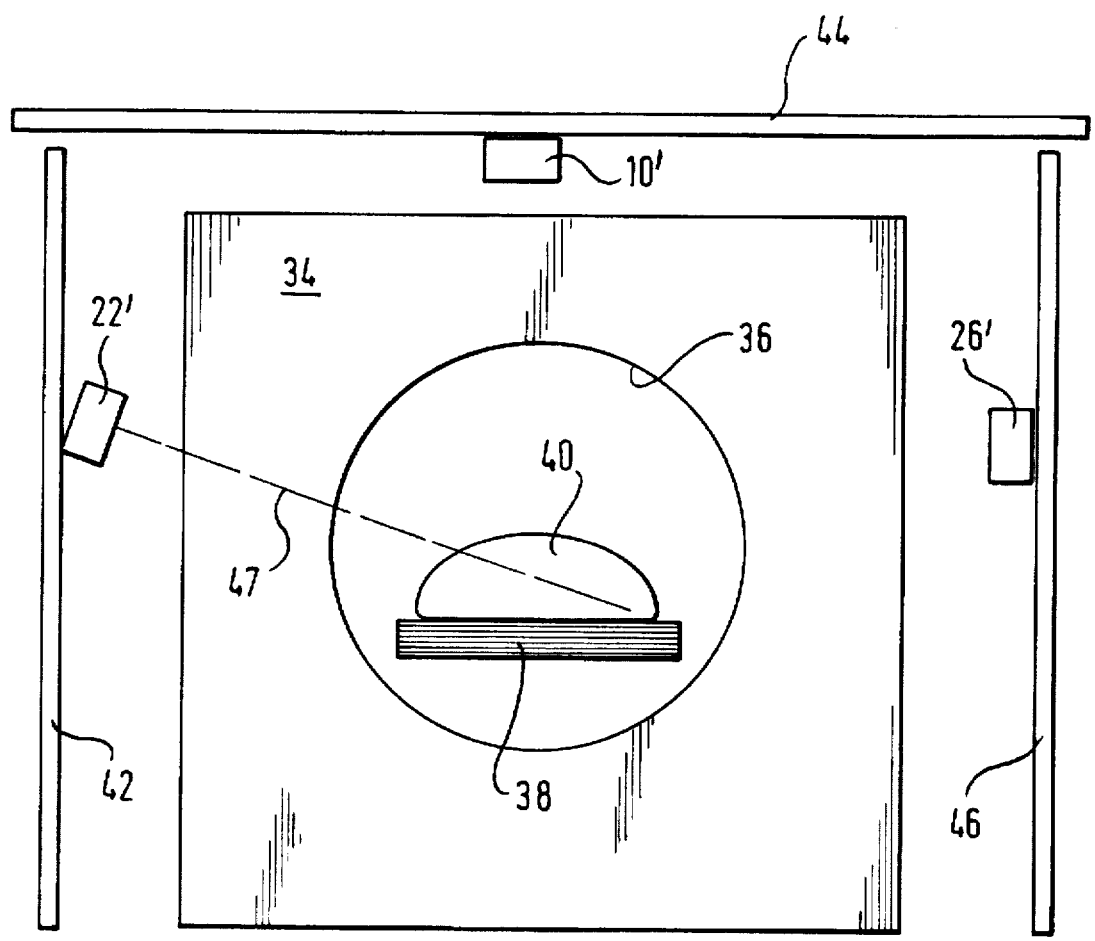
FIG. 3 is a schematic view of pivotally arranged line lasers in combination with a computer tomograph for conducting the method for marking a radiation zone.
Figure 4:
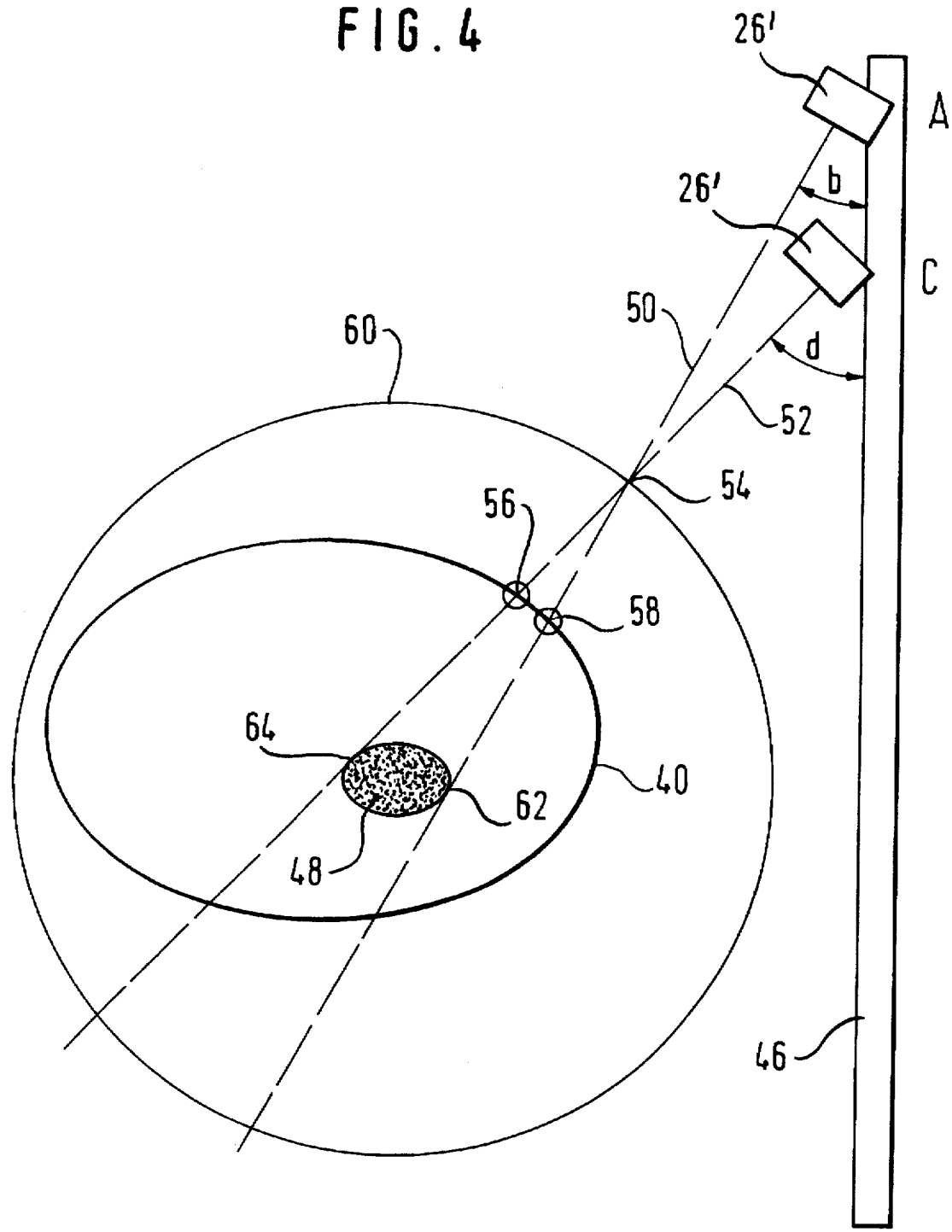
FIG. 4 is a graph schematically showing the principle of the method for marking a radiation zone.

A further arrangement of line lasers which are pivotally arranged in addition to be travelled is shown in FIGS. 3 and 4. FIG. 3 shows a CT 34 comprising an entry 36 accommodating a table 38 on which a patient 40 has been placed. The table can be vertically and longitudinally moved. Line lasers 10', 22' and 26' each are mounted to one of three linear rails 42, 44 and 46 which are arranged bridge-like in an orthogonal system around the CT. The line lasers 10', 22' and 26' are pivotally arranged around a plane defined by the rails 42, 44 and 46 as this is indicated for the line laser 22' and a beam 47 extending in the transverse plane. In contrast to the line lasers shown in FIG. 1, the line lasers are adapted to generate beam planes intersecting each other under an angle different from 90°.

FIG. 4 shows the rail 46 including the line laser 26' which can be moved along the rail 46 taking two different positions A and C as shown. In the position A the line laser 26' defines a pivotal angle with respect to the rail 46, while in the position C there is a pivotal angle d. The laser beams are directed towards a tumor 48 of a patient 40. A pair of beams 50 and 52 being part of the beam planes each generated by the laser being located in the positions A and C and extending within a transverse plane intersecting the tumor 48 intersect each other in a point 54 and enter the patient 40 at the points 56 and 58. The intersection 54 is located on a circle 60 along which the focus of a radiation device (not shown) may be moved. The center of the flying circle 60 coincides with the center of the tumor 48. Line laser beam 50 is oriented such that its prolongation is tangent to the tumor 48 at a location 62, and the line laser beam 52 is oriented such that its prolongation is tangent to the tumor at a further location 64.

Subsequently, the method for positioning and marking a patient at diagnostic devices in utilizing the devices shown in FIGS. 1 and 2 will be explained. In an initial position, the sagittal laser 12 is arranged in the center, while both the side lines 28, 30 are located in a defined zero position. The transverse line 18 extends a predetermined distance from the transverse axis of the CT not shown. As already mentioned the laser lines intersect in a virtual isocenter. The patient may be oriented with respect to these lines to be moved to the CT. In a previous diagnosis the position and extension of the tumor has been determined. Now the patient lying on the table will be moved outwardly by means of the controller of the CT until the center of the tumor is located in the plane of the transverse line 18. Both the remaining coordinates of the center of the tumor (X and Y) resulting from the CT will be supplied to the input device 32, whereby the laser lines 20, 28, 30 are moved to the positions as commanded by the input. The spatial coordinate network of laser lines projected onto the body of the patient indicates the location of the center of the tumor which may be marked on the patient to accomplish a reproducible orientation with respect to the isocenter of the radiation device.

By the input of further parameters and coordinates the lines may be further moved to indicate the geometric extension of the tumor on the skin. For this, one is particularly concerned with the extension of the tumor within the vertical intersecting plane of the CT (projection of the geometric data onto the skin surface) on the one hand and the entry field for the radiation which is determined by the divergence of the radiation device and the distance between the focus and the skin on the other hand. From the input data defining these coordinates and the parameters of the radiation device (divergence and distance), the controller determines the positions to which the beams have to be traveled. The lines projected on the skin will be used for further marking the patient.

Now, the method for marking a radiation zone in using the apparatus shown in FIGS. 3 and 4 will be explained. After the location and the extension of the tumor 48 of the patient 40 has been determined by the CT 34, the table and the position of the lasers will be varied such that the center of the tumor 48 lies within the coordinates of the center point of the focus flying circle 60 of the radiation device to be positioned later. Thus the tumor takes the isocenter of the radiation device. The line laser 26' will be now used to mark the skin area of the patient 40 which shall be subjected to the radiation beams according to a previously accomplished therapy planning. For this, the line laser 26' will be moved and pivoted such that it emits a beam 50 within the transverse plane defined by the focal flying circle which beam coincides with a desired boundary beam of the radiation beams, i.e. the beam 50 extends through the focus 54 and its prolongation is tangent to the tumor 48 at the location 62. Thereafter, the line laser 26' will be moved and pivoted to generate a further beam 52 defining the other desired boundary beam of the radiation beams within the transverse plane, this being obtained by the beam 52 intersecting alike the focus 54 and its prolongation being tangent to the tumor 48 at another location 64. The line laser beams 50, 52 enter the skin of the patient at the points 56 and 58 where the boundary beams of the radiation will impact afterwards the skin within the selected transverse plane. The points 56 and 58 are located within projecting lines which are projected on the skin by the beam planes of the line lasers 26'. The points 56 and 58 are defined by intersections of these marking lines with the transverse plane. For identifying the points 56, 58 the transverse plane may be displayed by a further line laser (not shown) generating a transverse line. The intersections 56, 58 projected on the skin will be used for marking the patient.

I claim:

1. A method of marking a patient for a radiation treatment of a zone of said patient, said treatment using a radiation source having a focus, a selectable angle of divergence and an isocenter about which said radiation source can be rotated in a vertical plane, with said focus thus describing a circle, with said method including the following steps:

determining the coordinates of the location and extension of said radiation zone of said patient by means of a computer tomograph;

selecting the direction of said radiation with respect to the body of said patient and said divergent angle;

positioning said patient such that said center of said radiation zone coincides with said isocenter;

generating a first laser beam by a line laser which is vertically displaceable and rotatable about a horizontal axis, said line laser being adjusted such that said laser beam intersects said focus and is tangent to said radiation zone on one side;

marking the line thus projected on the skin of said patient;

projecting a second laser beam by said line laser or a second line laser such that its beam intersects said focus and is tangent to said radiation zone on the opposite side; and marking the second line thus projected on said skin of said patient.

2. A method for marking a patient for radiation treatment comprising the steps of:

(a) placing a patient in need of radiation treatment on a table;

(b) determining the distance between a focus of radiation beams of a radiation device and a center of a radiation zone to be applied to said patient, the radiation direction and divergence of said radiation beams;

(c) generating a first laser beam by a line laser and adjusting said line laser vertically and horizontally until said first laser beam intersects said focus of radiation beams and is tangent to said radiation zone;

(d) generating a second laser beam by a second line laser and adjusting said second line laser vertically and horizontally until said second laser beam intersects said focus of radiation tangent to said radiation zone at a different location from said first laser beam; and (e) applying marking on the skin of said patient along the laser lines projected onto the skin of said patient to generate two visible lines on the skin thereof.

3. The method of claim 2, including the step of indicating a plane defined by both the line laser beams on the skin of the patient by a third marking line generated by one of said line lasers, said third marking line intersecting said other marking lines.

4. The method of claim 2, including the step of pivoting the line lasers about an axis parallel to the sagittal axis of said patient.

5. The method of claim 2, including the step of rotating the line lasers about an axis extending parallel to the line beams in the line beam plane.

* * * * *